United States Patent [19]

Baasner et al.

[11] Patent Number: 5,066,681
[45] Date of Patent: Nov. 19, 1991

[54] 1-TRIFLUOROMETHYL-1-NITRO-2-ALKOXY-2-ARYL-ETHANES, THEIR PREPARATION AND ANTIMYCOTIC AGENTS CONTAINING THEM

[75] Inventors: Bernd Baasner; Gunther Beck; Helmut Heitzer, all of Leverkusen; Klaus Scaller, Wuppertal, all of Fed. Rep. of Germany

[73] Assignee: Bayer Aktiengesellschaft, Leverkusen, Fed. Rep. of Germany

[21] Appl. No.: 409,909

[22] Filed: Sep. 20, 1989

[30] Foreign Application Priority Data

Oct. 8, 1988 [DE] Fed. Rep. of Germany ....... 3834326

[51] Int. Cl.$^5$ ..................... C07C 205/31; A01N 33/20
[52] U.S. Cl. .................................. 514/716; 514/699; 548/705; 568/424; 568/583
[58] Field of Search .................. 568/583, 424, 705; 514/716, 699

[56] References Cited

U.S. PATENT DOCUMENTS 4,778,935 10/1988 Beck ..................... 568/705

*Primary Examiner*—Robert Gerstl
*Attorney, Agent, or Firm*—Sprung Horn Kramer & Woods

[57] ABSTRACT

1-Trifluoromethyl-1-nitro-2-alkoxy-2-aryl-ethanes of the formula

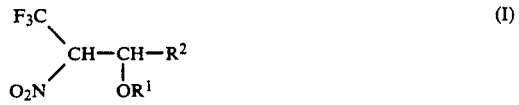

in which
$R^1$ represents a straight-chain or branched alkyl radical and
$R^2$ represents an optionally substituted aryl or hetaryl radical, their preparation from an aldehyde of the formula $R^2$-CHO, an alcohol of the formula $R^1$-OH and trifluoromethylnitromethane in the presence of a compound containing basic groups and antimycotic agents containing these compounds.

4 Claims, No Drawings

1-TRIFLUOROMETHYL-1-NITRO-2-ALKOXY-2-ARYL-ETHANES, THEIR PREPARATION AND ANTIMYCOTIC AGENTS CONTAINING THEM

The present invention relates to new 1-trifluoromethyl-1-nitro-2-alkoxy-2-aryl-ethanes of the formula (I)

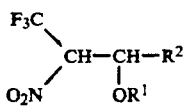

in which
- $R^1$ represents a straight-chain or branched alkyl radical and
- $R^2$ represents an optionally substituted aryl or hetaryl radical.

Preferably, $R^1$ represents a straight-chain or branched alkyl radical having 1 to 6 C atoms. Methyl, ethyl, i-propyl, n-butyl, i-butyl and t-butyl are particularly preferred.

If $R^2$ contains heteroatoms, these may be, for example, 1 or 2 nitrogen, oxygen and/or sulphur atoms. If $R^2$ contains substituents, these may be, for example, 1 to 3 halogen atoms, in particular fluorine and/or chlorine atoms, 1 or 2 nitro groups, 1 or 2 alkoxy groups, in particular $C_1$- to $C_6$-alkoxy groups, 1 or 2 CHO groups or a radical of the type

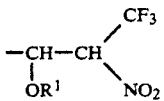

$R^1$ has the abovementioned meaning.

Preferably, $R^2$ is a 5- or 6-membered, carbocyclic or heterocyclic aryl radical, in particular a phenyl or thiazole radical.

Preferably, the aryl radical $R^2$ contains substituents. Preferred substituents are a fluorine atom, 1 to 3 chlorine atoms, a nitro group, a methoxy group, a CHO group or a radical of the type

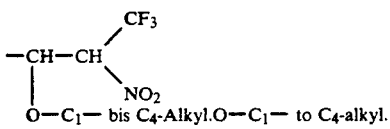

Particularly preferred $R^2$ radicals are: dichlorothiazolyl, 3- and 4-nitrophenyl, 4-methoxyphenyl, 4-formylphenyl, 2-, 3- and 4-chlorophenyl, 3,4- and 2,5-dichlorophenyl, 2,4,5-trichlorophenyl, 2-fluorophenyl and radicals of the type

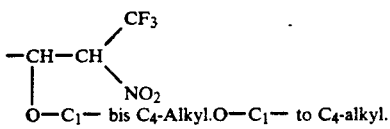

The compounds of the formula (I) have two asymmetric C atoms. They can therefore occur in the R,R, R,S, S,R and S,S form and in any mixtures of two, three or all of these forms.

The present invention relates to the compounds of the formula (I) in each case both in the individual forms (R,R, R,S, S,R or S,S form) and in any mixtures of two, three or all of these forms.

In such mixtures, for example, an arbitrary first component (R,R, R,S, S,R or S,S form) may be present in a proportion from 1 to 70% by weight and, making up to 100%, a second or a second and third or a second, third and fourth component. Preferably, such mixtures contain all four components, i.e. the R,R, R,S, S,R and S,S form of a compound of the formula (I), each of these components preferably being present in an amount between 15 and 35% by weight and the total of all components making 100% by weight.

The composition of an existing mixture of optical isomers of a compound of the formula (I) may be altered in a manner known per se. For example, a deprotonation may be carried out, followed by a protonation, preferably at temperatures in the range −90 to −100° C. using glacial acetic acid. Chromatographic methods may also be used. Pure optical isomers of compounds of the formula (I) may likewise also be obtained from mixtures of optical isomers in a manner known per se, for example by liquid chromatography (LC).

The present invention furthermore relates to a process for the preparation of 1-trifluoromethyl-1-nitro-2-alkoxy-2-aryl-ethanes of the formula (I)

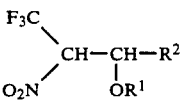

in which
- $R^1$ represents a straight-chain or branched alkyl radical and
- $R^2$ represents an optionally substituted aryl radical optionally containing heteroatoms, which is characterized in that an aldehyde of the formula (II)

$$R^2-CHO \quad (II)$$

in which
$R^2$ has the meaning indicated in formula (I),
is reacted with an alcohol of the formula (III)

$$R^1-OH \quad (III)$$

in which
$R^1$ has the meaning indicated in formula (I), and trifluoromethylnitromethane in the presence of a compound containing basic groups.

Preferably and particularly preferably, those aldehydes of the formula (II) and those alcohols of the formula (III) are employed in which $R^2$ or $R^1$ have the meanings designated above as preferred and particularly preferred. The compounds containing basic groups may be, for example, ammonia, primary, secondary or tertiary amines, ammonium acetate or amino acids. Examples of amines are pyridine and piperidine. Preferably, 3-aminopropionic acid (=β-alanine) is employed.

The starting materials may be employed, for example, in those amounts in which 0.8 to 1.5 moles of an alcohol of the formula (III), at least 1 mole of trifluoromethylnitromethane and 0.1 to 2 moles of the compound containing basic groups are used per equivalent of aldehyde groups which are contained in the compound of the formula (II). Preferably, 1 to 1.2 moles of an alcohol of the formula (III), 1 to 1.8 moles of trifluoromethylnitromethane and 0.8 to 1.2 moles of the compound containing basic groups are employed per equivalent of aldehyde groups which are contained in the The reaction according to the invention is generally carried out in the presence of an organic solvent. Such solvents may be inert solvents, for example benzene or toluene, but an excess above the amount of the alcohol of the formula (III) necessary for the reaction may also be used.

Since extraneous solvents have to be separated from the reaction mixture again in a separate step and alcohols of the formula (III) are generally easily and economically accessible, the reaction is preferably carried out without extraneous solvents and using excess alcohol.

The process according to the invention may be carried out at different temperatures, for example at those in the range −50 to +100° C. Preferred temperatures are in the range 0 to 50° C., particularly preferred are those in the range 15 to 30° C. At higher temperatures, for example above 30° C. and, in particular, above 50° C., shorter reaction times can, admittedly, be used, but then impairments generally have to be expected with respect to the selectivity.

Suitable reaction times are, for example, those between an hour and a week. When working at temperatures in the range 0 to 30° C., good results are generally obtained with reaction times from 10 to 50 hours. Optimum reaction times can be determined by following the course of the reaction by gas chromatography and, for example, discontinuing the reaction when aldehyde of the formula (II) is no longer present in the reaction mixture or when a particularly favourable ratio of 1-trifluoromethyl-1-nitro-2-alkoxy-2-aryl-ethane of the formula (I) formed to by-products and starting materials which may still be present exists.

Working-up of the reaction mixture can be carried out in various ways. For example, the compound containing basic groups or transformation products thereof can first be filtered off, the filtrate can be concentrated and the residue which remains can be further purified by recrystallization, distillation and/or chromatographic methods. For example, the reaction mixture can also be stirred into water. If the desired reaction product is then present as a solid, this can be filtered off and further purified by recrystallization, distillation and/or chromatographic methods. If the desired reaction products after stirring into water is present as an oil, this can be taken up using a solvent, for example methylene chloride, and, for example, purified by chromatographic means.

The 1-trifuoromethyl-1-nitro-2-alkoxy-2-arylethanes of the formula (I) according to the invention surprisingly show an antimycotic action, for example against dermatophytes, yeasts and hyphomycetes. The present invention therefore also relates to antimycotic agents, which are characterized in that they contain 1-trifluoromethyl-1-nitro-2-alkoxy-2-aryl-ethanes of the formula (I) and, if appropriate, customary additives, and a process for combating undesired fungi, which is characterized in that 1-trifluoromethyl-1-nitro-2-alkoxy-2-aryl-ethanes of the formula (I), if appropriate together with customary additives, are allowed to act on undesired fungi or places threatened by them.

EXAMPLES

Example 1

60.0 g (0.427 mol) of 4-chlorobenzaldehyde, containing 0.427 equivalents of aldehyde groups, were dissolved in 400 ml of methanol and first 67 g (0.52 mol) of trifluoromethylnitromethane and then 38.0 g (0.427 mol) of β-alanine were added to the solution. The reaction mixture was then stirred at 22° C. for 24 hours. For working-up, the solid constituents were separated by filtration and washed with methanol, and the filtrate and the washing fluid was combined and concentrated in vacuo. An oily mixture with crystalline components remained. The crystalline components was separated by filtering again and washed with methanol, and the filtrate and the washing liquid were again concentrated in vacuo. 88.1 g of crude product were obtained which had the following composition according to gas chromatographic analysis:

40.5% by weight of 4-chlorobenzaldehyde,
13.4% by weight of 4-chlorobenzaldehyde dimethyl acetal and
43.2% by weight of 1-trifluoromethyl-1-nitro-2-methoxy-2-p-chlorophenyl-ethane (diastereomer mixture 12.1+31.1% by weight).

This crude product was separated by chromatography on 800 g of silica gel using petroleum ether/methylene chloride (1:1) as eluent. 36.8 g of 1-trifluoromethyl-1-nitro-2-methoxy-2-p-chlorophenyl-ethane (diastereomer mixture) were obtained as a first fraction as a yellow oil having a refractive index of nD20: 1.4770. According to gas chromatographic determination, this product had a purity of 96.9%. Based on reacted 4-chlorobenzaldehyde, the yield was thus 60.4% of theory.

In a repeat of this reaction, in which, however, the mixture was stirred at 22° C for 96 hours, an identical product was obtained after working-up by chromatography in a yield of 88.5%, based on reacted 4-chlorobenzaldehyde.

EXAMPLES 2 to 18

The procedure was as in Example 1, with a reaction time of 24 hours, but the alcohols and aldehydes employed were varied. In individual cases, another eluent was also used. The details of the examples carried out are evident from Table 1. In Table 1, in the column "R²"

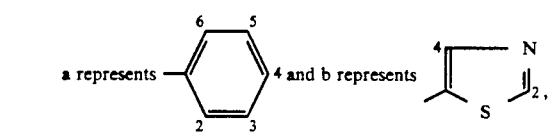

in the column "Eluent", A represents methylene chloride/petroleum ether 1:1, B represents methylene chloride/petroleum ether 3:1, C represents toluene/ethyl acetate 1:1 and D represents toluene and in the column "Characterization of the reaction product", IR represents characteristic IR bands in cm$^{-1}$.

TABLE 1

| Example No. | Starting materials R¹ | of the formulae (II) and (III) and reaction product of the formula (I) with R² | Eluent | Characterization of the reaction product | Yield of purified product (% of theory) based on reacted starting material of the formula (II) |
|---|---|---|---|---|---|
| 2 | CH₃ | a 4-NO₂ | A | Melting point: 105° C. | 77 |
| 3 | CH₃ | a 3-NO₂ | A | IR: 1591, 1530, 1360, 1265, 1182, 1148, 1112, 884, 781, 740, 698, 682 | 63 |
| 4 | CH₃ | a 4-CHO | B | IR: 1702, 1580, 1372, 1335, 1265, 1210, 1184, 1145, 1109, 1073, 888, 832, 772, 721 | 47 |
| 5 | CH₃ | a 3.4-Di-Cl | A | IR: 1580, 1472, 1374, 1325, 1259, 1213, 1179, 1142, 1108, 785 | 81 |
| 6 | CH₃ | a 4-Cl | A | IR: 1573, 1495, 1362, 1325, 1259, 1217, 1189, 1143, 1109, 887, 832, 780 | 60.4 |
| 7 | CH₃ | a 2.4-Di-Cl | A | IR: 1579, 1477, 1366, 1324, 1260, 1211, 1186, 1140, 1108, 797 | 79 |
| 8 | CH₃ | a 3-Cl | A | IR: 1576, 1370, 1326, 1259, 1216, 1189, 1145, 1110, 796, 780, 710, 692 | 82 |
| 9 | CH₃ | a 2-Cl | A | IR: 1578, 1370, 1329, 1261, 1213, 1188, 1146, 1107, 783, 760 | 67 |
| 10 | CH₃ | a 2.6-Di-Cl | A | Boiling point: 145° at 22 mbar (after chromatography) | 58 |
| 11 | n-Butyl | a 4-NO₂ | | Melting point: 72° C.*⁾ | 61 |
| 12 | CH(CH₃)₂ | a 4-NO₂ | B | Melting point: 94° C.*⁾ | 58 |
| 13 | n-Butyl | b 2.4-Di-Cl | D | IR: 1580, 1515, 1422, 1366, 1321, 1257, 1197, 1093, 1064, 896 | 67 |
| 14 | CH(CH₃)₂ | b 2.4-Di-Cl | B | Melting point: 75° C. | 48 |
| 15 | CH₃ | a 2-F | A | IR: 1578, 1495, 1462, 1369, 1330, 1263, 1189, 1145, 1107, 887, 764 | 73 |
| 16 | CH₃ | a 4-CHO | B | Melting point: 170–172° C. | 53 |
| 17 | CH₃ | a 3-CHO | A | IR: 1580, 1372, 1355, 1326, 1266, 1211, 1190, 1153, 1097, 892, 851, 769, 719 | 66 |
| 18 | n-Butyl | a 4-CHO | | Melting point: 157° C.*⁾ | 71 |

*⁾These products were not chromatographed, but recrystallized from petroleum ether.

EXAMPLE 19

Test for antimycotic activity

The in vitro tests were carried out in serial dilution tests in which the influence of the tested substances on inoculations of micro-organisms in various media was investigated and in each case the minimum inhibitory concentration of the tested substances was determined.

Micro-organisms used were:

As an example of dermatophytes:

A Trichophyton mentagrophytes.

As a medium for this, so-called Kimmig broth (5 g of glycerol, 13 g of nutrient broth, 8.6 g of Bacto Repton, 9.0 g of NaCl and 10 g of glucose mixed with 1 l of demineralized water) was used. In this medium 1 × 10⁵ micro-organisms of A per ml were employed and incubated for 5 days at 28° C.

As an example of hyphomycetes:

B Aspergillus fumigatus.

The same medium, the same amount of microorganisms and the same incubation temperature were used as in A. The incubation time was 4 days. As examples of yeasts:

C Candida albicans.

As a medium for this, yeast nitrogen base (Difco) was used. In this medium, 1 × 10⁴ micro-organisms of C per ml were employed and incubated for 3 days at 37° C.

D Torulopsis glabrata.

The same medium, the same amount of microorganisms, the same incubation period and the same incubation temperature were used as in C.

The results are compiled in Table 2

TABLE 2

| | Minimum inhibitory concentration (μg/ml) for micro-organisms of | | | |
|---|---|---|---|---|
| Tested substance | A | B | C | D |
| from Example 5 | 2 | 8 | <1 | <1 |
| from Example 6 | 1 | 16 | 2 | <1 |
| from Example 7 | 4 | 64 | 4 | <1 |
| from Example 8 | 2 | 8 | 2 | <1 |

What is claimed is:

1. 1-Trifluoromethyl-1-nitro-2-alkoxy-2-arylethanes of the formula (I)

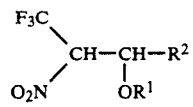

(I)

in which

R¹ represents a straight-chain or branched alkyl radical having 1 to 6 C-atoms and R² represents an unsubstituted phenyl radical or phenyl radical substituted by 1 to 3 halogen atoms, 1 or 2 nitro groups, 1 or 2 alkoxy groups, 1 or 2 CHO groups or a radical of the type

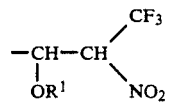

in which $R^1$ has the meaning indicated in formula (I), as substituents.

2. 1-Trifluormethyl-1nitro-2-alkoxy-2-arylethanes of claim 1 in which $R^2$ is an unsubstituted phenyl radical.

3. An antimycotic agent, which contains an effective amount of 1-trifluoromethyl-1-nitro-2-alkoxy-2-arylethanes of the formula (I) as in claim 1, and, if appropriate, customary additives.

4. The method of combating undesired fungi, which comprises applying to such fungi or to a locus from which it is desired to exclude such fungi an effective amount of a 1-trifluoromethyl-1-nitro-2-alkoxy-2-arylethane of the formula (I) as in claim 2, if appropriate, together with customary additives.

* * * * *

UNITED STATES PATENT AND TRADEMARK OFFICE
CERTIFICATE OF CORRECTION

PATENT NO. : 5,066,681
DATED : November 19, 1991
INVENTOR(S) : Baasner et al.

It is certified that error appears in the above-identified patent and that said Letters Patent is hereby corrected as shown below:

Title Page      [75] Inventors:   Delete " Scaller " and substitute -- Schaller --

Col. 3, line 4   After " the " insert -- compound of the formula (II). --

Col. 8, line 1   Delete " claim 1 " and substitute -- claim 2 --

Signed and Sealed this

Twenty-first Day of September, 1993

Attest:

BRUCE LEHMAN

Attesting Officer     Commissioner of Patents and Trademarks